US008485983B2

(12) United States Patent
Gouma et al.

(10) Patent No.: US 8,485,983 B2
(45) Date of Patent: Jul. 16, 2013

(54) SELECTIVE NANOPROBE FOR OLFACTORY MEDICINE

(75) Inventors: Pelagia-Irene Gouma, Port Jefferson, NY (US); Sanford R. Simon, Stony Brook, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 1895 days.

(21) Appl. No.: 11/351,171

(22) Filed: Feb. 9, 2006

(65) Prior Publication Data

US 2006/0277974 A1 Dec. 14, 2006

Related U.S. Application Data

(63) Continuation-in-part of application No. 10/419,349, filed on Apr. 21, 2003, now Pat. No. 7,017,389.

(51) Int. Cl.
*A61B 5/08* (2006.01)
*G01N 33/497* (2006.01)

(52) U.S. Cl.
USPC .......................................... 600/532; 73/23.3

(58) Field of Classification Search
USPC ............ 600/529–543, 484, 595, 587; 73/23.3
See application file for complete search history.

(56) References Cited

U.S. PATENT DOCUMENTS

| | | | |
|---|---|---|---|
| 3,953,173 A | 4/1976 | Obayashi et al. | |
| 4,007,063 A | 2/1977 | Yasuda et al. | |
| 4,030,340 A | 6/1977 | Chang | |
| 4,140,106 A * | 2/1979 | Kirmaier | 600/532 |
| 4,169,369 A | 10/1979 | Chang | |
| 4,430,191 A | 2/1984 | Sone et al. | |
| 4,481,499 A | 11/1984 | Arima et al. | |
| 4,753,916 A * | 6/1988 | Carcia et al. | 502/321 |
| 4,823,803 A * | 4/1989 | Nakamura | 600/530 |
| 5,037,525 A * | 8/1991 | Badwal | 204/421 |
| 5,055,441 A * | 10/1991 | McCarron et al. | 502/321 |
| 5,252,292 A | 10/1993 | Hirata et al. | |
| 5,531,225 A * | 7/1996 | Nawata et al. | 600/532 |
| 5,546,004 A | 8/1996 | Schmelz | |
| 5,624,640 A * | 4/1997 | Potthast et al. | 422/90 |
| 5,783,154 A * | 7/1998 | Althainz et al. | 422/98 |
| 5,811,662 A | 9/1998 | Williams et al. | |
| 5,858,186 A | 1/1999 | Glass | |
| 5,969,231 A | 10/1999 | Qu et al. | |
| 5,993,625 A | 11/1999 | Inoue et al. | |
| 6,173,602 B1 | 1/2001 | Moseley | |
| 6,173,603 B1 | 1/2001 | Horn | |

(Continued)

OTHER PUBLICATIONS

Wang et al, "An integrated array of multiple thin-film metal oxide sensors for quantification of individual components in organic vapor mixtures", 1993, Sensors and Actuators B, 13-14, 458-461.*

(Continued)

*Primary Examiner* — Navin Natnithithadha
(74) *Attorney, Agent, or Firm* — Medlen & Carroll, LLP (57) ABSTRACT

An apparatus is for detecting the presence of selected gaseous compounds indicative of a medical condition includes a probe having one or more sensor elements having a conductivity which is responsive to the presence of selected gaseous compounds, at least one sensor element containing a transition metal oxide selected from the group consisting of $WO_3$, beta-$MoO_3$ and $UO_2$; and means for measuring the conductivity of each said sensor element.

10 Claims, 9 Drawing Sheets

U.S. PATENT DOCUMENTS

| | | | |
|---|---|---|---|
| 6,319,724 B1 | 11/2001 | Lewis et al. | |
| 6,411,905 B1 | 6/2002 | Guoliang et al. | |
| 6,467,333 B2 | 10/2002 | Lewis et al. | |
| 6,606,566 B1 | 8/2003 | Sunshine | |
| 6,609,068 B2 | 8/2003 | Cranley et al. | |
| 6,620,109 B2 | 9/2003 | Hanson, III | |
| 6,660,231 B2 | 12/2003 | Moseley | |
| 6,703,241 B1 | 3/2004 | Sunshine et al. | |
| 6,767,732 B2 | 7/2004 | Alocija et al. | |
| 6,820,012 B2 | 11/2004 | Sunshine | |
| 6,839,636 B1 | 1/2005 | Sunshine et al. | |
| 6,841,391 B2 | 1/2005 | Lewis et al. | |
| 6,981,947 B2 * | 1/2006 | Melker | 600/532 |
| 7,017,389 B2 | 3/2006 | Gouma | |
| 7,101,340 B1 | 9/2006 | Braun | |
| 7,104,963 B2 * | 9/2006 | Melker et al. | 600/532 |
| 7,220,387 B2 | 5/2007 | Flaherty et al. | |
| 7,687,275 B2 * | 3/2010 | Burdinski | 436/116 |
| 7,704,214 B2 * | 4/2010 | Abraham-Fuchs et al. | 600/532 |
| 7,950,271 B2 * | 5/2011 | Novak et al. | 73/31.06 |
| 2003/0008407 A1 | 1/2003 | Fu | |
| 2008/0077037 A1 | 3/2008 | Gouma et al. | |
| 2011/0061446 A1 | 3/2011 | Gouma et al. | |

OTHER PUBLICATIONS

Gouma, P. I.., et al. *Selective nanoprobes for 'signalling gases'* Nanotechnology 17 (2006) S48-S53.

Imawan et al., "Gas-sensing characteristics of modified-$MoO_2$ thin films using Ti-overlayers for $NH_3$ gas sensors", Sensors and Acutators B 64 (2000) pp. 193-197.

Imawan et al., "A new preparation method for sputtered $MoO_3$ multilayers for the application in gas layers", Sensors and Acutators B 78 (2001) pp. 119-125.

Ferroni et al., "Nanosized thin films of tungsten-titanium mixed oxides as gas sensors", Sensors and Actuators B 58 (1999) pp. 289-294.

Chung et al., "Gas sensing properties of $WO_3$ thick film for $NO_2$ gas dependent on process condition", Sensors and Actuators B 60 (1999) pp. 49-56.

Marquis et al., "A semiconducting metal oxide sensor array for the detection of $NO_x$ and $NH_3$", Sensors and Actuators B 77 (2001) pp. 100-110.

Sberveglieri et al., "$WO_3$ sputtered thin films for $NO_x$ monitoring", Sensors and Actuators B 26 (1995) pp. 89-92.

Livage et al., "Encapsulation of biomolecules in silica gels", J. Phys.: Condens. Matter 13 (2001) pp. R673-R691.

Dai, L. et al., Sensors and sensor arrays based on conjugated polymers and carbon nanotubes; Pure Appl. Chem.., vol. 74, No. 9, pp. 1753-1772, 2002.

Gouma, P. et al., Novel materials and applications of electronic noses and tongues; MRS. Bulletin/Oct. 2004, pp. 697-702.

Pardo, M. et al., Electronic olfactory systems based on metal oxide semiconductor sensor arrays; MRS Bulletin/Oct. 2004, pp. 703-708.

Dutta, R. et al., Classification of ear, nose and throat bacteria using a neuralnetwork-based electronic nose; MRS Bulletin/Oct. 2004, pp. 709-713.

Suslick, K., An optoelectronic nose: "seeing" smells by means of colorimetric sensor arrays; MRS Bulletin/Oct. 2004, pp. 720-725.

Ryan, M. et al., Polymer-carbon black composite sensors in an electronic nose for air-quality monitoring; MRS Bulletin/Oct. 2004, pp. 714-719.

Winquist, F. et al., Electronic tongues; MRS Bulletin/Oct. 2004, pp. 726-731.

Kearney, D. et al., Breath ammonia measurement in *Helicobacter pylori* infection; Digestive Diseases and Sciences, vol. 47, No. 11, Nov. 2002, pp. 2523-2530.

Romagnuolo, J. et al., Using breath tests wisely in gastroenterology...; Am. J. of Gastro., vol. 97, No. 5, pp. 1113-1126, 2002.

Kearney, D.J. et al, Breath ammonia measurement for diagnosis of *Helicobacter pylori* infection: A preliminary study; Diag. and Socio-Eco. Gen. Prac., Sep. 2001, pp. A99-A100.

\* cited by examiner

The apparatus described herein employs a probe having at least one sensor with a transition metal oxide which has a conductivity selectively changeable in response to the presence of particular analytes. The change in conductivity is believed to result from red-ox reactions occurring at the surface of the oxide. Preferably, an array of sensors with different transition metal oxides is employed in the probe. Each sensor produces a characteristic response to particular analytes. The individual sensor together represent a signature response which can be analyzed by appropriate algorithms to determine the presence and amounts of particular analytes. This data, in turn, provides information about the medical condition of the subject.

In an embodiment of the invention, at least one sensor includes tungsten trioxide, $WO_3$, as the transition metal oxide. The $WO_3$ can have a monoclinic or orthorhombic crystal structure. Preferably, additional sensors are employed in the probe to provide an array. Non-limiting examples of other transition metal oxides which can be employed include molybdenum trioxide, $MoO_3$, which can be orthorhombic (alpha-$MoO_3$) or monoclinic (beta-$MoO_3$), titanium dioxide ($TiO_2$), tin oxide ($SnO_2$), chromium oxides ($CrO_2$, $Cr_2O_3$), iridium oxide ($IrO_2$) and manganese dioxide (beta-$MnO_2$), either individually or in physical combination.

The metal oxides used in the present invention are preferably binary metal oxides that may be classified into three groups according to their crystallographic characteristics. The gases detected by these metal oxides are oxidizing or reducing gases similarly fall into three groups.

The first group of metal oxides, classified herein as "rutile structured" metal oxides, possess a rutile structure similar to that found in titanium dioxide ($TiO_2$). The rutile structure is tetragonal, but in some cases it has been described as a distorted hexagonal close packed oxide array with half the octahedral sites occupied by the metal. Alternative rows of octahedral sites are full and empty. The rutile structure is regarded as an ionic structure. Examples of rutile structured metal oxides include $TiO_2$, $SnO_2$, $CrO_2$, $IrO_2$ and beta-$MnO_2$, etc.

The second group of metal oxides, classified herein as "rhenium oxide structured" or $ReO_3$ type metal oxides, possess a cubic structure similar to that found in rhenium oxide, which is closely related to the structure found in perovskite ($CaTiO_3$). The unit cell of the crystal contains metal atoms at the corners with oxygen at the center edges. Metal oxides which have this structure include $WO_3$, beta-$MoO_3$, and $UO_2$ and possess a monoclinic crystal structure.

The third group of metal oxides are classified herein as "alpha-$MoO_3$ type" metal oxides. And have a unique, weakly bonded 2D layered structure. Alpha-$MoO_3$ is a typical representative of this group and possess an orthorhombic crystal structure.

Gases which may be detected in accordance with the present invention may similarly be placed into three categories. Type I gases are nitrogen-lacking reducing gases including, but not limited to, CO alcohols and hydrocarbons. Type II gases are nitrogen-containing reducing gases including, but not limited to, ammonia and amines. Finally, Type III gases are oxidizing gases including, but not limited to, oxygen, and oxides of nitrogen such as, NO, $NO_2$, etc.

It has been found that rutile structured metal oxides are selective in their sensitivity to the nitrogen-lacking reducing gases (Type I), the rhenium oxide $ReO_3$ type metal oxides are selective in their sensitivity to the oxidizing gases (Type III) and the alpha-$MoO_3$ type metal oxides are selective in their sensitivity to the nitrogen-containing reducing gases (Type II).

The detection process of oxidizing/reducing gases by semiconducting metal oxides involves the change in the conductivity of the oxide in the presence of the gas due to catalytic red-ox reactions occurring at the oxides' surfaces. These catalytic reactions are controlled by the electronic structure of the oxide system used as well as by the chemical composition, crystal structure, and relative orientation of the surfaces of the oxide phase(s) exposed to the gas.

Considering other oxides isostructural with $MoO_3$, but with higher stability at high temperature exposures, tungsten oxides have been identified as promising candidates. Contrary to what was expected, the orthorhombic phase of $WO_3$ did not respond to the presence of ammonia but was very sensitive to $NO_2$ (see FIG. 2). The reason for this apparent discrepancy in the gas sensing properties of the respective polymorphs of these two oxides is believed to lie in their crystallographic differences and the specific sensing mechanism that each favors. Whereas α-$MoO_3$ has a layered structure with (010) basal plane that is built up of double chains of edge-sharing $[MoO_6]$ octahedra connected through vertices, the orthorhombic $WO_3$ is structurally similar to the $ReO_3$ type structure of monoclinic $MoO_3$ (β-phase). $WO_3$ is selective to $NO_2$ and similar behavior has been observed for β-$MoO_3$ (as shown below). An adsorption (chemisorption) based sensing mechanism is active in this case that does not affect the bonds in the metal oxide surface.

The crystal structure of $WO_3$ is a distortion of rhenium oxide cubic structure in which tungsten atoms are located in cube corners and the oxygen atoms are located on the cube edges. Each tungsten atom is surrounded by six oxygen atoms forming an octahedron. The slight rotation of these octahedral with respect to each other, as well as unequal bond lengths in the octahedral coordination, causes lattice distortion and reduces the symmetry. The distorted structure is stable in several forms giving rise to different phases depending on the temperature. Thus $WO_3$ exists in various polymorphic forms. There are at least 7 known polymorphic transformations in the temperature range of 0 to 1220° K. In bulk crystals, the triclinic phase is stable below 17° C., the monoclinic phase is stable between 17-320° C. and the orthorhombic is stable from 320-720° C. above which tetragonal phase is the dominant phase. Stoichiometric $WO_3$ readily loses oxygen to form $WO_{3-x}$. When oxygen is removed from the lattice in sufficient amounts, some of the octahedral change their character from corner-sharing to edge-sharing. In slightly reduced $WO_3$, shear planes are introduced in many directions at irregular intervals.

Semiconducting metal oxides show surface sensitivity to redox reactions involving gases. For example, during hydrocarbon oxidation reactions, hydrogen abstraction occurs at (001) and (100) crystal phases of $MoO_3$ while oxygen addition occurs at the (010) basal plane. The local environment of active sites (available for gas adsorption, hydrogen extraction, or oxygen addition) and the orientation of the surface containing these active sites, vary for different phases of a given system, and thus the catalytic behavior of these phases is variable. Oxygen basicity is found to increase with decreasing Mo—O bond strength occurring at different surfaces. Surface oxygen vacancies formed under reduction conditions may influence gas adsorption processes. They may result in slightly reduced metal oxide surfaces which undergo re-oxidation by gaseous oxygen (adsorption-based sensing) or they may order and give rise to crystallographic shear structures that accommodate non-stoichiometric metal oxide compositions known as Magnéli phases (reaction-based sensing). The presence of ordered vacancies and crystallographic shear structures provides a mechanism for selective oxidation.

Considering the two main polymorphs of $MoO_3$, the α-phase (orthorhombic) has a layered structure with (010) basal plane which is built up of double chains of edge-sharing $[MoO_6]$ octahedral connected through vertices while the β-phase (monoclinic) has a $ReO_3$-type structure. The $ReO_3$ type structure does not contain the Van der Waals gap of the α-$MoO_3$. Therefore, α-$MoO_3$ upon reduction in catalysis forms the $Mo_{18}O_{52}$ structure instead of the $ReO_3$ type $Mo_8O_{23}$ shear structure. It was discussed above that the α-phase is selective to ammonia and highly sensitive to amines (which are moderate bases) and the sensing mechanism is consistent with the reduction of $MoO_3$ and the formation of ordered phases, which suggests reaction-based sensing process. Thus, it seems that ammonia and amines can be best sensed by "loosely bound" layered oxide structures, such as the orthorhombic α-$MoO_3$ phase that enable the reaction of lattice oxygen with the gas and provide easy mechanisms for accommodating the off-stoichiometric M:O ratio. On the other hand, oxidizing gases, such as $NO_2$, may be easily adsorbed on $ReO_3$-type crystals. Oxidizing gases destroy oxygen defects.

CO and hydrocarbons typically react with adsorbed oxygen from the environment and may be sensed by rutile-type structures, such as the polymorphs of $SnO_2$ and $TiO_2$. Since a given crystal structure may be sensitive to more than one gases, sensing tests at different temperatures need to be carried out so as to identify the optimum operating temperature for the specific sensor. It is important to remain within the phase stability field of the particular polymorph of the oxide. As discussed above, phase stability depends on the grain/particle size of the sensing element (oxide crystal), the operating temperature and pressure conditions, and the presence of impurities and these are some critical factors to consider when selecting a sensor material.

Metal oxide films can be made in various ways. In one embodiment of the invention a sol-gel route is employed wherein the isopropoxide of the metals (e.g., molybdenum isopropoxide, tungsten isopropoxide, etc.) is mixed with an alkanol (e.g., propanol, butanol, etc.) to form a sol-gel of the corresponding oxide (e.g., $MoO_3$, $WO_3$, etc.). The sol-gels are amorphous colloidal solutions. Such sol-gels can be made in accordance with methods described in U.S. patent application Ser. No. 10/419,349.

In another embodiment of the invention, hybrid films of sol-gel $MoO_3$ and flame sprayed rutile ($TiO_2$) powders can be prepared.

In yet another embodiment of the invention a hydrothermal method of preparing, e.g., $WO_3$, chilled solutions of an alkali metal salt of the transition metal oxygenate (e.g., sodium molybdate, sodium tungstate, etc.) are acidified, preferably with a mineral acid such as hydrochloric acid, to provide the hydrated corresponding transition metal acid (e.g., molybdic acid, tungstic acid, etc). Preferably, the temperature of the alkali metal salt solution and the acid are both at the same temperature and both between 0° C. and about 20° C., preferably between 0° C. and about 10° C., and more preferably between 0° C. and about 5° C. The precipitated transition metal acid is then separated, for example by centrifugation, filtration and the like, then washed, dried and calcined to provide the crystal structure.

Orthorhombic and monoclinic phases of $WO_3$ can be obtained by varying the calcining temperature. The dried, calcined metal oxides are preferably mixed with a vehicle (e.g., butanol, or other alkanol) then spun coated onto a sensor substrate.

Figure 7:
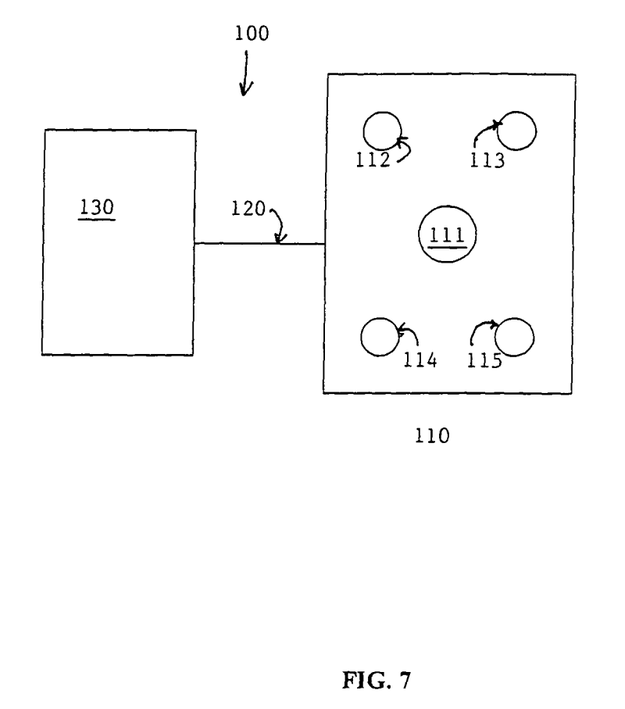

Referring now to FIG. 7, an apparatus 100 for detecting the presence of selected gaseous compounds is schematically illustrated wherein probe 110 is electrically connected to an analyzer 130 via electrical cable line 120. Probe 110 includes at least one sensor element 111 containing a transition metal oxide selected from the group consisting of monoclinic or orthorhombic $WO_3$, monoclinic beta-$MoO_3$ and $UO_2$. Preferably, however, the probe 110 also includes a plurality of sensor elements 112, 113, 114, 115, containing different transition metal oxides such as orthorhombic alpha-$MoO_3$, $TiO_2$, combined $MoO_3$—$TiO_2$, $V_2O_5$, $Cr_2O_3$, $In_2O_3$, $SnO_2$, $MnO_2$, etc. Analyzer 130 determines the electrical conductivity of each sensor element individually by conventional means. The multiple sensor elements provide a characteristic output signature for different analytes. Analyzer 130 also preferably includes pattern recognition algorithms wherein the signature of the analyte being detected is compared with known signatures stored in memory for known analytes. Various algorithms and computer controlled systems for olfactometry are known and disclosed for example in U.S. Pat. Nos. 6,411,905, 6,606,566, 6,609,068, 6,620,109, 6,839,636, 6,767,732 and 6,820,012, which are herein incorporated by reference The following examples illustrate the invention.

EXAMPLES

Metal Oxide films of 150-200 nm thickness were prepared by deposition of the transition metal oxide on alumina substrates containing interdigitated gold or platinum electrodes. A gas flow bench was used for single sensor tests and a modified e-nose chamber for the sensor array studies.

The films were observed under SEM under room temperature condition, after heat treatments to 500° C. for different times. X-ray diffraction (XRD) patterns were recorded using a PW 1729 Philips X-ray diffractometer.

Sensing experiments were carried out in the temperature range of 200° C. to 500° C. and the gas sensitivities were plotted. The gas sensitivity S was calculated according to the following formula:

$$S=(R_{Air}-R_{Gas})/R_{Air}$$

wherein $R_{Air}$ is the electrical resistance of the transition metal oxide film in the presence of air.

$R_{Gas}$ is the electrical resistance of the transition metal oxide film in the presence of a gas containing the target analyte.

Example 1

Figure 1:
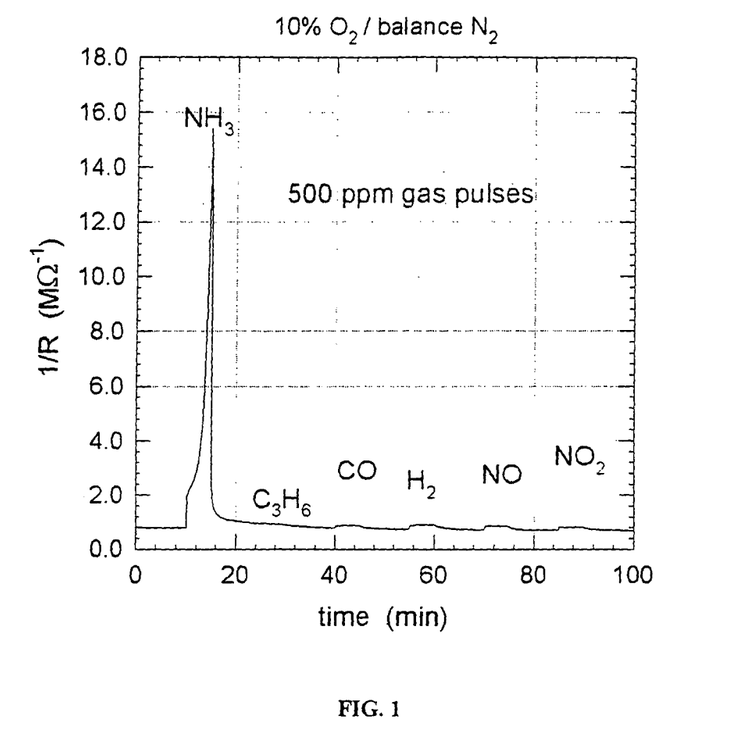

A sensor was fabricated from orthorhombic alpha-$MoO_3$ placed in a chamber and sequentially subjected to $NH_3$, $C_3H_6$, CO, $H_2$, NO, and $NO_2$ as target analytes. The conductivity of the sensor was measured as each of the analytes was pulsed into the chamber. The results were plotted in FIG. 1, which shows the highly selective responsiveness of the alpha-$MoO_3$ sensor to ammonia and the flat response (non-responsiveness) of the sensor to the other target analytes. This Example demonstrates the ability of the alpha-$MoO_3$ to selectively detect ammonia and other nitrogen containing reducing gases in the presence of hydrocarbons, hydrogen, and oxides of carbon and/or nitrogen.

Example 2

Figure 2:
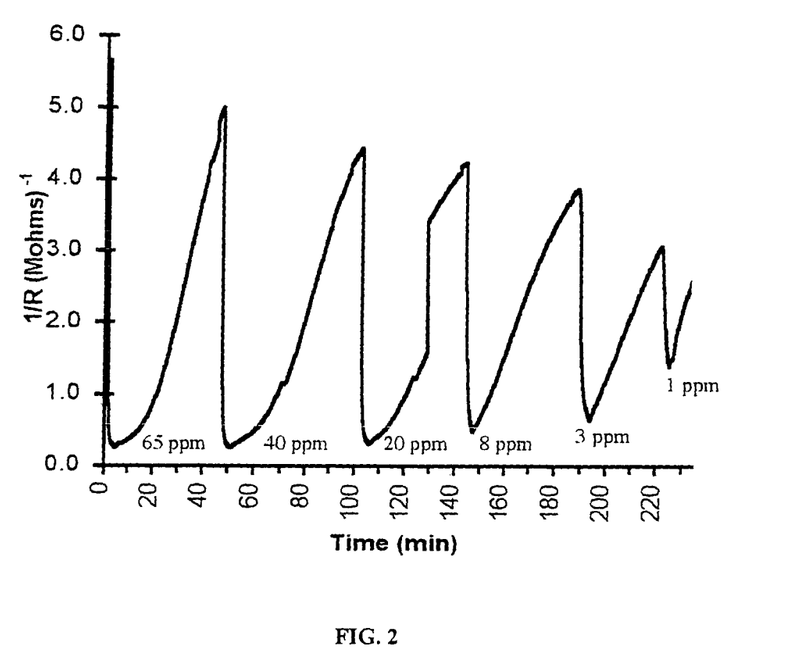

A sensor was fabricated from orthorhombic $WO_3$ placed in a chamber and subjected to the target analytes as in Example 1. Surprisingly, the orthorhombic $WO_3$ did not respond to the presence of ammonia but did selectively respond to nitrogen oxides. Nitrogen oxide was then pulsed into the chamber at various concentrations and the conductivity of the sensor was measured. The results are shown in FIG. 2, which illustrates the sensitivity of the sensor to concentrations of nitrogen oxide as low as 1 ppm.

While not wishing to be bound by any theory, it is believed that the orthorhombic $WO_3$ differs in selectivity from orthorhombic $MoO_3$ because of the crystallographic differences. Whereas orthorhombic $MoO_3$ has a layered structure with a (010) basal plane built up of double chains of edge-sharing $[MoO_6]$ octahedra connected through vertices, the orthorhombic $WO_3$ is structurally similar to the monoclinic beta-$MoO_3$. Both beta-$MoO_3$ and orthorhombic $WO_3$ are selective to nitrogen-containing oxidizing gases.

Example 3

Figure 3:
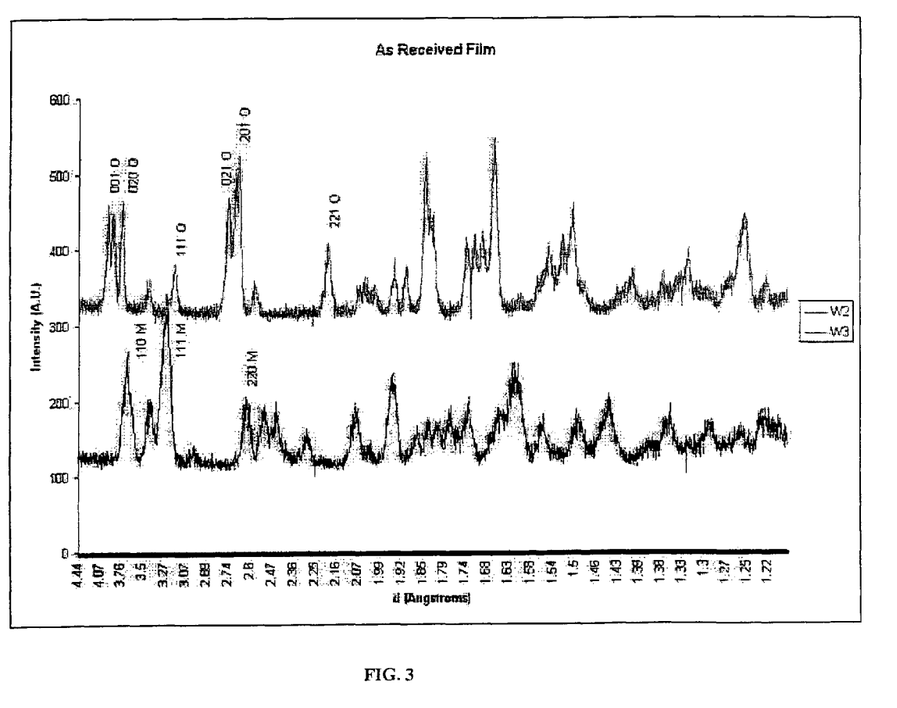
Figure 4:
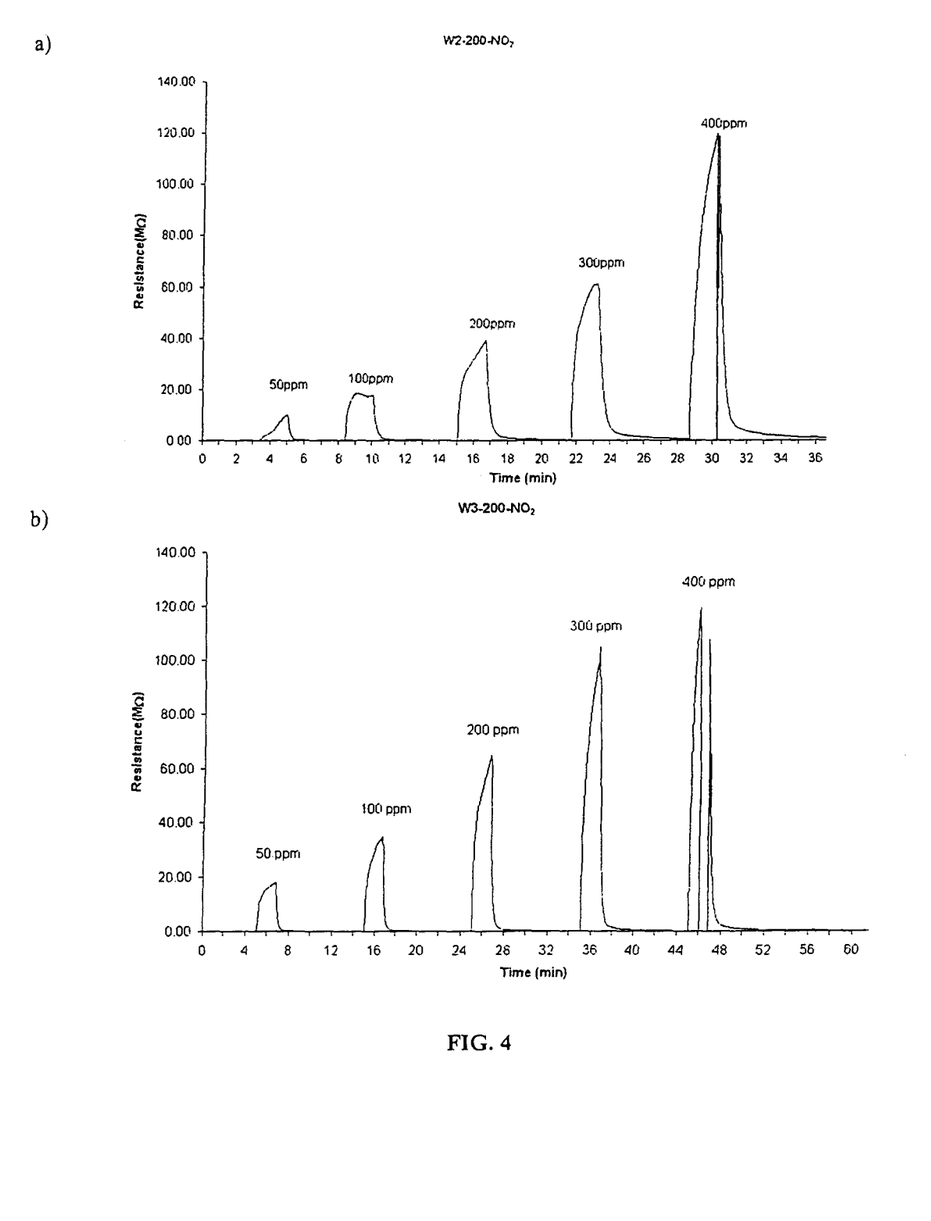

Monoclinic $WO_3$ (designated as W2 and which appears as the lower graph) and orthorhombic $WO_3$ (designated as W3, and which appears as the upper graph) were tested for responsiveness to $NO_2$. FIG. 3 shows X-ray diffraction spectra for both of these polymorphs of $WO_3$ at room temperature. Sensors were fabricated from both polymorphs and exposed to varying concentrations of $NO_2$ ranging from 50 ppm to 400 ppm which were pulsed into the chamber in which the sensors were positioned. FIG. 4 shows the responsiveness to $NO_2$ for both the monoclinic $WO_3$ (upper W2 graph) and orthorhombic $WO_3$ (lower W3 graph). As can be seen, both polymorphs of $WO_3$ responded to $NO_2$.

Example 4

A probe was fabricated with a five sensor array containing monoclinic $MoO_3$ at position (1), orthorhombic $MoO_3$ at position (2), orthorhombic $WO_3$ at position (3), and two hybrid $TiO_2$—$MoO_3$ sensors, i.e., $TiO_2$-monoclinic $MoO_3$ and $TiO_2$-orthorhombic $MoO_3$ at positions (4) and (5), respectively.

Figure 5A:
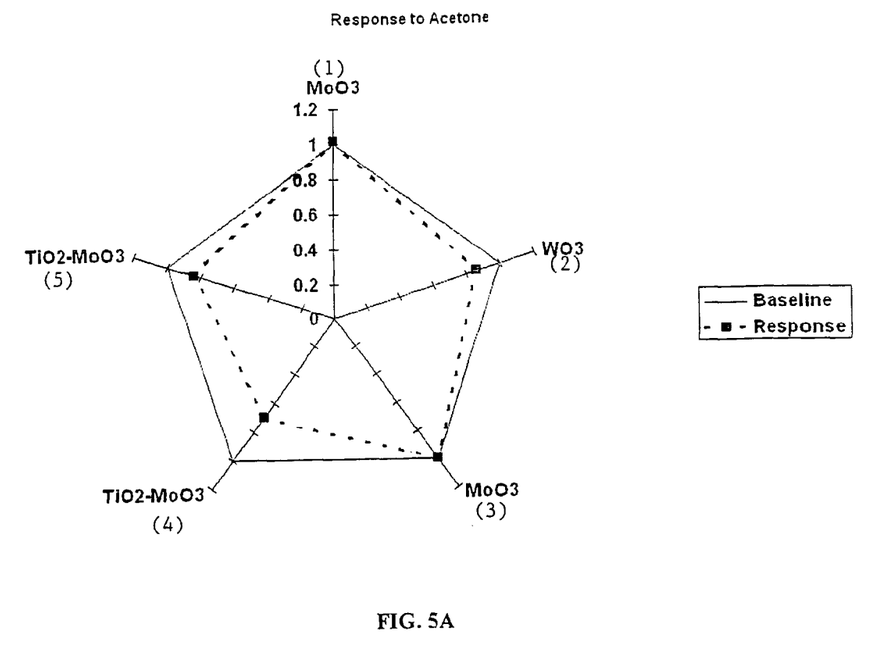
Figure 5B:
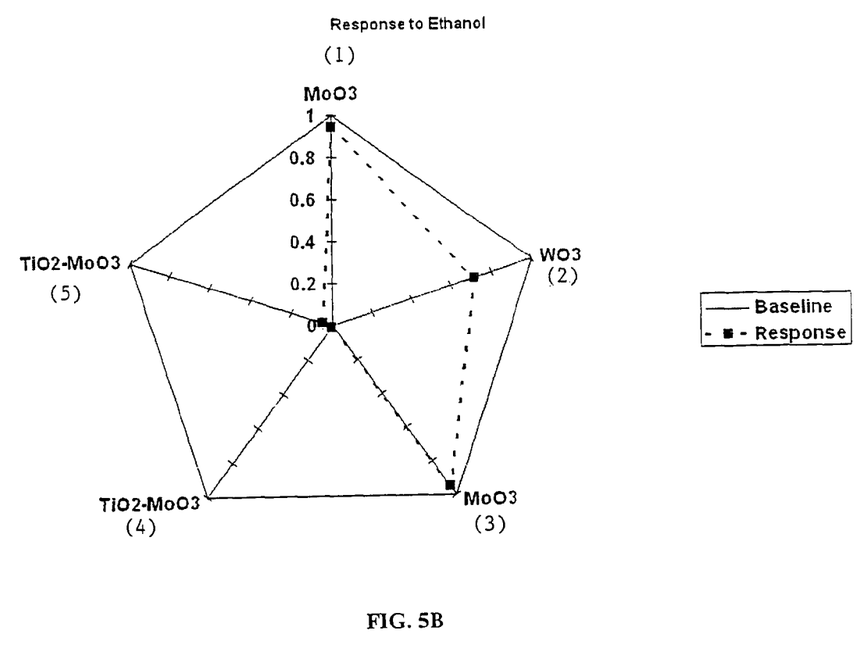

The probe was tested for responsiveness to acetone and ethanol. FIG. 5A is a plot showing the pattern response of the five sensor array to acetone. The $MoO_3$ sensors demonstrated no sensitivity. The $WO_3$ sensor displayed some sensitivity and the hybrid $TiO_2$—$MoO_3$ sensors displayed sensitivity to acetone. FIG. 5B shows a pattern response of the five sensor array to exposure to ethanol. As can be seen, the $MoO_3$ sensors displayed no sensitivity. The $WO_3$ sensor exhibited a noticeable response to ethanol and the hybrid $TiO_2$—$MoO_3$ sensors exhibited great sensitivity to ethanol.

Example 5

Figure 6A:
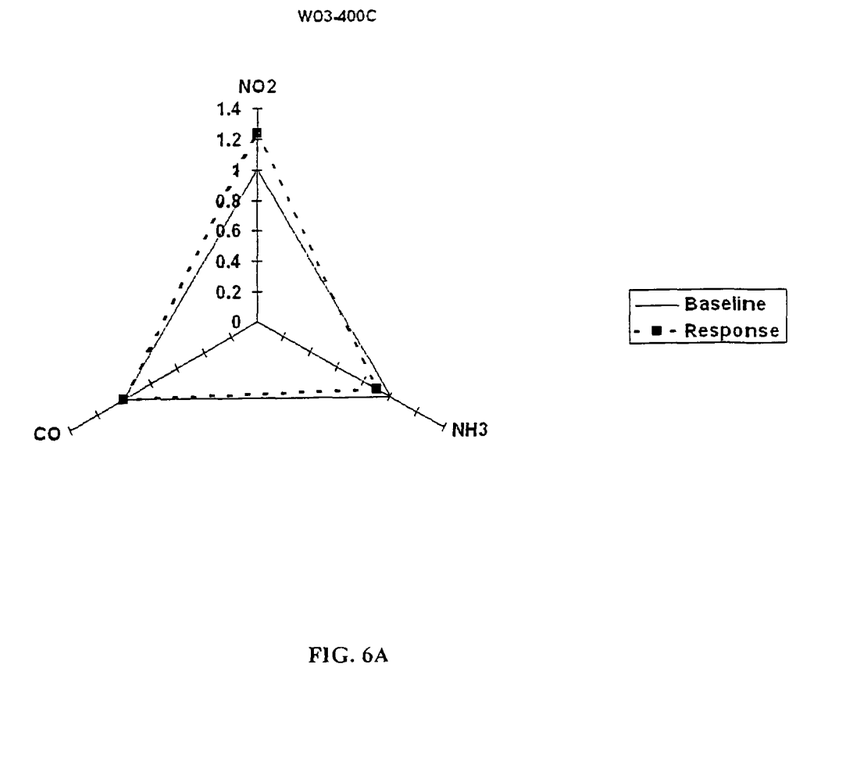
Figure 6B:
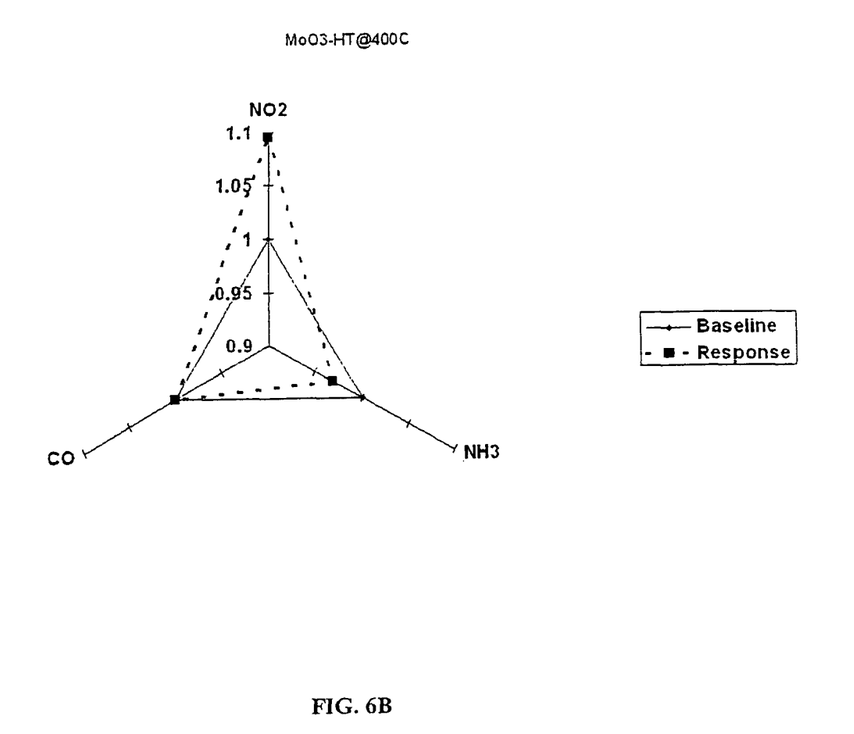

Sensors fabricated from orthorhombic $WO_3$ and monoclinic $MoO_3$ were subjected to exposure to $NO_2$, $NH_3$ and CO at 400° C. The responses were measured and plotted in FIGS. 6A and 6B. As can be seen from FIG. 6A, the $WO_3$ sensor was selectively responsive to $NO_2$ but not $NH_3$ or CO. FIG. 6B shows that monoclinic $MoO_3$ is highly responsive to $NO_2$ but less responsive to $NH_3$ and non-responsive to CO.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method for diagnosing a medical condition in a subject, said method comprising the steps of:
   a) providing an apparatus for selectively detecting a presence of a gaseous compound in a mixture of gases, wherein said apparatus comprises a probe, said probe comprising:
      i) a first sensor responsive to the presence of a gaseous oxidizing compound, a second sensor responsive to a gaseous reducing compound containing no nitrogen, and a third sensor responsive to a gaseous reducing compound containing nitrogen, each said sensor comprising an undoped crystalline form of a transition metal oxide disposed within said sensor in a thin film of said crystals to create in said thin film an electrical property that is selectively responsive to said gaseous compound, wherein said crystals in said first sensor comprise rhenium oxide structured crystals, said crystals in said second sensor comprise rutile structured crystals, and said crystals in said third sensor comprise $\alpha MoO_3$-structured crystals, and
      ii) an analyzer, wherein said analyzer is electrically connected to each of said sensors such that said analyzer measures changes in said electrical property of each said sensor;
   b) exposing the probe to a breath of the subject, and
   c) using the analyzer to determine the presence in the breath of the subject of one or more of said gaseous compounds, wherein said presence is indicative of said medical condition of the subject.

2. The method of claim 1 wherein said transition metal oxides in said first sensor are selected from the group consisting of one or more of $WO_3$, $\beta MoO_3$ and $UO_2$.

3. The method of claim 2 wherein the $WO_3$ is monoclinic.

4. The method of claim 2 wherein the $WO_3$ is orthorhombic.

5. The method of claim 1 wherein said transition metal oxides in said second sensor are selected from the group consisting of one or more of $TiO_2$, $SnO_2$, $CrO_2$, $InO_2$, and $\beta MnO_2$.

6. The method of claim 1 wherein said transition metal oxide in said third sensor is $\alpha MoO_3$.

7. The method of claim 6 wherein said $\alpha MoO_3$ is combined with one or more transition metal oxides selected from group consisting of one or more of $TiO_2$, $V_2O_5$, $Cr_2O_3$, $In_2O_3$, $In_3O_4$, $SnO_2$ and $MnO_2$.

8. The method of claim 1 wherein each probe in the apparatus contains different transition metal oxides or physical combinations thereof, such that (i) each said probe exhibits a different characteristic response to each of a selection of gaseous compounds, and (ii) comparing the responses with predetermined responses to the selected gaseous compounds provides an indication of the medical condition of the subject.

9. The method of claim 1 wherein the medical condition comprises one or more of dental pathology, cardiovascular disease, diabetes, nephritis, bilirubin production, blood cholesterol level, liver function impairment and renal disease.

10. The method of claim 1 wherein the analyzer comprises a computer.

* * * * *